United States Patent [19]

Rowe, deceased et al.

[11] Patent Number: Plant 6,779

[45] Date of Patent: May 2, 1989

[54] CHRYSANTHEMUM PLANT NAMED RYFLASH

[75] Inventors: Frank Rowe, deceased, late of Wellington; by Philip M. B. Rowe, executor, Wellington; by Derek A. Rowe, executor, Taunton; by Theodore H. Harding, executor, Wellington, all of England

[73] Assignee: Fides Beheer B.V., De Lier, Netherlands

[21] Appl. No.: 141,532

[22] Filed: Jan. 7, 1988

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Ryflash having intense red ray floret color (upper surface), with the reverse side of the ray florets being generally gold. The mature disc florets are bright yellow, providing a distinct contrast with the ray florets.

1 Drawing Sheet

The present invention comprises a new and distinct cultivar of *Chrysanthemum morifolium,* hereinafter referred to by the cultivar name Ryflash.

Ryflash is a product of a planned breeding program, and was originated by Frank Rowe (deceased) from a hybridization made in a controlled breeding program in Wellington, Somerset, England in 1979. The male and female parents are not known at this time.

Ryflash was discovered and selected as one flowering plant within the progeny of the cross by Frank Rowe in approximately November 1979 in a controlled environment in Wellington, Somerset, England. The first act of asexual reproduction of Ryflash was accomplished when vegetative cuttings were taken by Frank Rowe from the initial selection in February 1980 in a controlled environment in Wellington, Somerset, England. Horticultural examination of subsequently selected units has demonstrated that the combination of characteristics as herein disclosed for Ryflash are firmly fixed and are retained through successive generations of asexual reproduction.

Ryflash has not been observed under all possible environmental conditions. The phenotype may vary significantly with variations in environment such as temperature, light intensity, and day length. The following observations, measurements and comparisons describe plants grown in Wellington, Somerset, England under greenhouse conditions which approximate those generally used in commercial practice.

The following traits have been repeatedly observed and are determined to be basic characteristics of Ryflash, which in combination distinguish this Chrysanthemum as a new and distinct cultivar:

1. The ray floret color, upper surface, is intense deep red. The under surface is generally gold.
2. Daisy or single type.
3. The petals have a velvet texture.
4. The disc florets when mature are yellow, thereby providing a center which has a sharp, pleasant contrast with the red floret color.
5. Heavy pollen.
6. Large dark leaves.

Of the many commercial cultivars known to the present inventor, the most similar in comparison to Ryflash is Red Tuneful. In comparison to Red Tuneful, Ryflash has larger flowers, more flowers, the flower color is a darker red, and larger leaves. The response, flower type, and disc floret color are similar to those same characteristics of Red Tuneful.

The accompanying photographic drawing shows typical inflorescence and foliage characteristics of Ryflash, with colors being as nearly true as possible with illustrations of this type.

In the following description, color references are made to The Royal Horticultural Society Colour Chart.

Classification:

*Botanical.*—*Chrysanthemum morifolium,* cv. Ryflash.

*Commercial.*—Cut spray.

INFLORESCENCE

A. Capitulum:
- *Form.*—Flat.
- *Type.*—Single.
- *Diameter across face.*—75–85 mm.

B. Corolla of ray florets:
- *Color (general tonality from a distance of three meters).*—Red.
- *Color (upper surface).*—46A.
- *Color (lower surface).*—Generally gold.

C. Corolla of disc florets:
- *Color (mature).*—Yellow.
- *Color (immature).*—Green.

D. Reproductive organs:
- *Androecium.*—Present only in disc florets; numerous.
- *Gynoecium.*—Present in both disc and ray florets; numerous.

PLANT

A. General appearance:
- *Height.*—85 cm.

B. Foliage:
- *Color (upper surface).*—137B.
- *Color (under surface).*—Lighter than 137B.
- *Shape.*—Pinnately lobed.

I claim:

1. A new and distinct Chrysanthemum plant named Ryflash, as illustrated and described, and parts thereof.

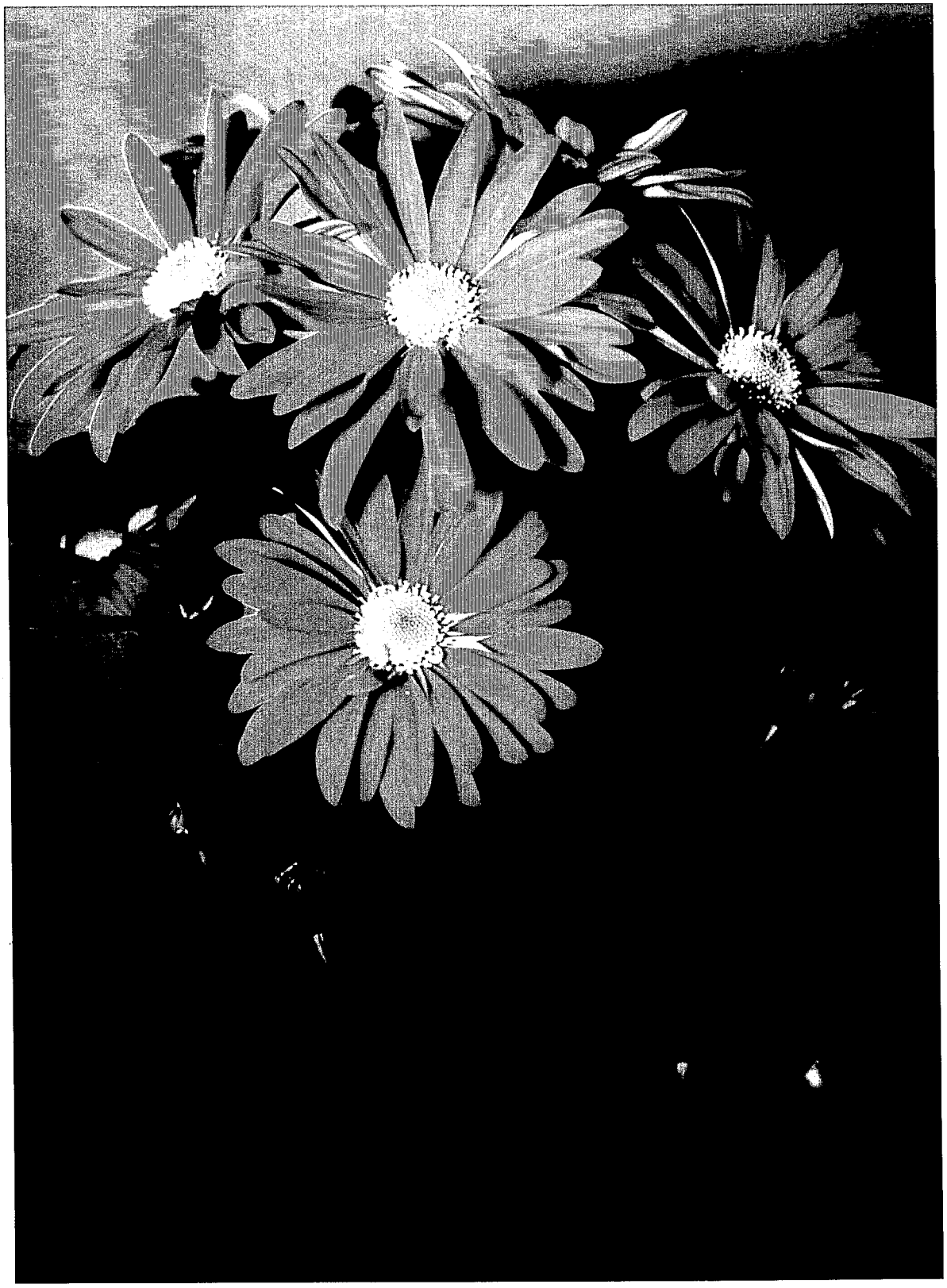

* * * * *